United States Patent
Han et al.

(10) Patent No.: US 12,145,133 B2
(45) Date of Patent: *Nov. 19, 2024

(54) METHOD FOR PREPARING DEHYDROGENATION CATALYST FOR LINEAR CHAIN LIGHT HYDROCARBONS WITH HIGH REGENERATION EFFICIENCY

(71) Applicant: Heesung Catalysts Corporation

(72) Inventors: Hyun-sik Han, Seoul (KR); Young-san Yoo, Gyeonggi-do (KR); Ho-dong Kim, Gyeonggi-do (KR); Hyun A Choi, Incheon (KR)

(73) Assignee: HEESUNG CATALYSTS CORPORATION, Gyeonggi-do (KR)

( * ) Notice: Subject to any disclaimer, the term of this patent is extended or adjusted under 35 U.S.C. 154(b) by 1415 days.

This patent is subject to a terminal disclaimer.

(21) Appl. No.: 16/611,061

(22) PCT Filed: Jan. 11, 2018

(86) PCT No.: PCT/KR2018/000514
§ 371 (c)(1),
(2) Date: Nov. 5, 2019

(87) PCT Pub. No.: WO2018/207992
PCT Pub. Date: Nov. 15, 2018

(65) Prior Publication Data
US 2020/0122125 A1    Apr. 23, 2020

(30) Foreign Application Priority Data

May 11, 2017    (KR) .................... 10-2017-0058603

(51) Int. Cl.
| | | |
|---|---|---|
| *B01J 23/62* | (2006.01) | |
| *B01J 35/61* | (2024.01) | |
| *B01J 35/63* | (2024.01) | |
| *B01J 35/64* | (2024.01) | |
| *B01J 37/02* | (2006.01) | |
| *B01J 37/08* | (2006.01) | |
| *B01J 37/16* | (2006.01) | |
| *C07C 5/32* | (2006.01) | |

(52) U.S. Cl.
CPC ........... *B01J 23/626* (2013.01); *B01J 35/613* (2024.01); *B01J 35/633* (2024.01); *B01J 35/647* (2024.01); *B01J 37/0201* (2013.01); *B01J 37/08* (2013.01); *B01J 37/16* (2013.01); *C07C 5/325* (2013.01); *C07C 2523/04* (2013.01); *C07C 2523/42* (2013.01)

(58) Field of Classification Search
CPC . C07C 5/325; C07C 2523/04; C07C 2523/42; B01J 23/626; B01J 37/08; B01J 37/16
See application file for complete search history.

(56) References Cited

U.S. PATENT DOCUMENTS

| | | |
|---|---|---|
| 4,716,143 A | 12/1987 | Imai |
| 4,717,779 A | 1/1988 | Bricker et al. |
| 4,786,625 A | 11/1988 | Imai et al. |
| 4,914,075 A | 4/1990 | Bricker et al. |
| 6,756,340 B2 * | 6/2004 | Voskoboynikov ....... B01J 21/04 502/328 |
| 8,993,474 B2 | 3/2015 | Choi et al. |
| 2003/0191351 A1 | 10/2003 | Voskoboynikov et al. |
| 2007/0123418 A1 | 5/2007 | Han |
| 2009/0275792 A1 | 11/2009 | Vogel |
| 2013/0261363 A1 | 10/2013 | Serban |
| 2014/0274673 A1 | 9/2014 | Kauffman et al. |
| 2014/0323785 A1 | 10/2014 | Lande |
| 2015/0158024 A1 | 6/2015 | Lande |
| 2018/0311645 A1 | 11/2018 | Han et al. |

FOREIGN PATENT DOCUMENTS

| | | |
|---|---|---|
| KR | 960013454 A | 5/1996 |
| KR | 20050009290 A | 1/2005 |
| KR | 20100078460 A | 7/2010 |
| KR | 101456900 B1 | 11/2014 |
| KR | 101527841 B1 | 6/2015 |
| KR | 20150116118 A | 10/2015 |
| KR | 101716170 B1 | 3/2017 |
| WO | WO 2018/207992 | 11/2018 |

OTHER PUBLICATIONS

Zangeneh et al., "The influence of solvent on the performance of Pt-Sn/θ-Al$_2$O$_3$ propane dehydrogenation catalyst prepared by co-impregnation method", Fuel Processing Technology, 109 (2013), pp. 118-123 (6 pages).
Wang et al., "Pt/Sn Intermetallic, Core/Shell and Alloy Nanoparticles: Colloidal Synthesis and Structural Control", Chemistry of Materials 25 (2013), pp. 1400-1407 (8 pages).
International Search Report and Written Opinion were mailed on May 17, 2018 by the International Searching Authority for International Application No. PCT/KR2018/000514, filed on Jan. 11, 2018 and published as WO 2018/207992 on (Applicant-Heesung Catalysts Corporation)(Original—7 pages// Translation—2 pages).
Jie Liu et al. "Effects of Al$_2$O$_3$ phase and Cl component on dehydrogenation of propane" vol. 368,(2016), pp. 233-240.

(Continued)

*Primary Examiner* — Sikarl A Witherspoon
(74) *Attorney, Agent, or Firm* — Ballard Spahr LLP

(57) ABSTRACT

The present invention relates to a catalyst used in a dehydrogenation reaction of a linear hydrocarbon gas in a range of C3 to C4, and provides a dehydrogenation catalyst which is deposited on a carrier obtained by changing the phase of platinum, an auxiliary metal and an alkali metal, wherein the platinum and the auxiliary metal are present as a single complex within a certain thickness from the outer edges of the catalyst in an alloy form.

9 Claims, 5 Drawing Sheets

(56) References Cited

OTHER PUBLICATIONS

Bhari Mallanna Nagaraja et al. "Effect of potassium addition on bimetallic PtSn supported θ-$Al_2O_3$ catalyst for n-butane dehydrogenation to olefins" Catalysis Today, vol. 232, (2014), pp. 40-52.

* cited by examiner

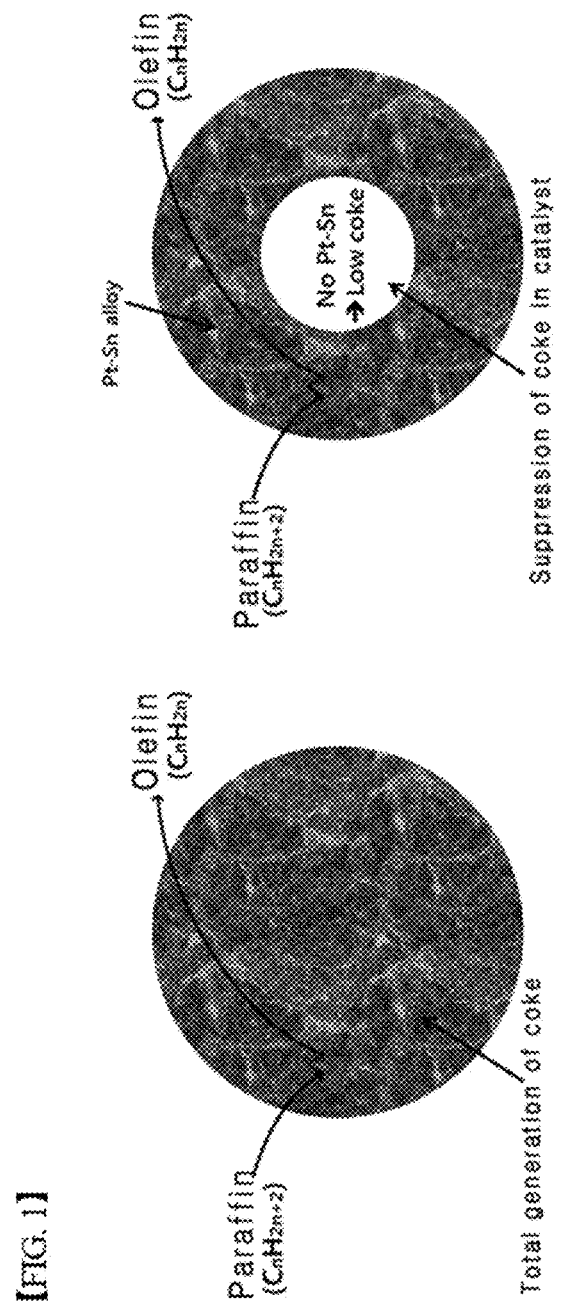
[FIG. 1]

[FIG. 2]
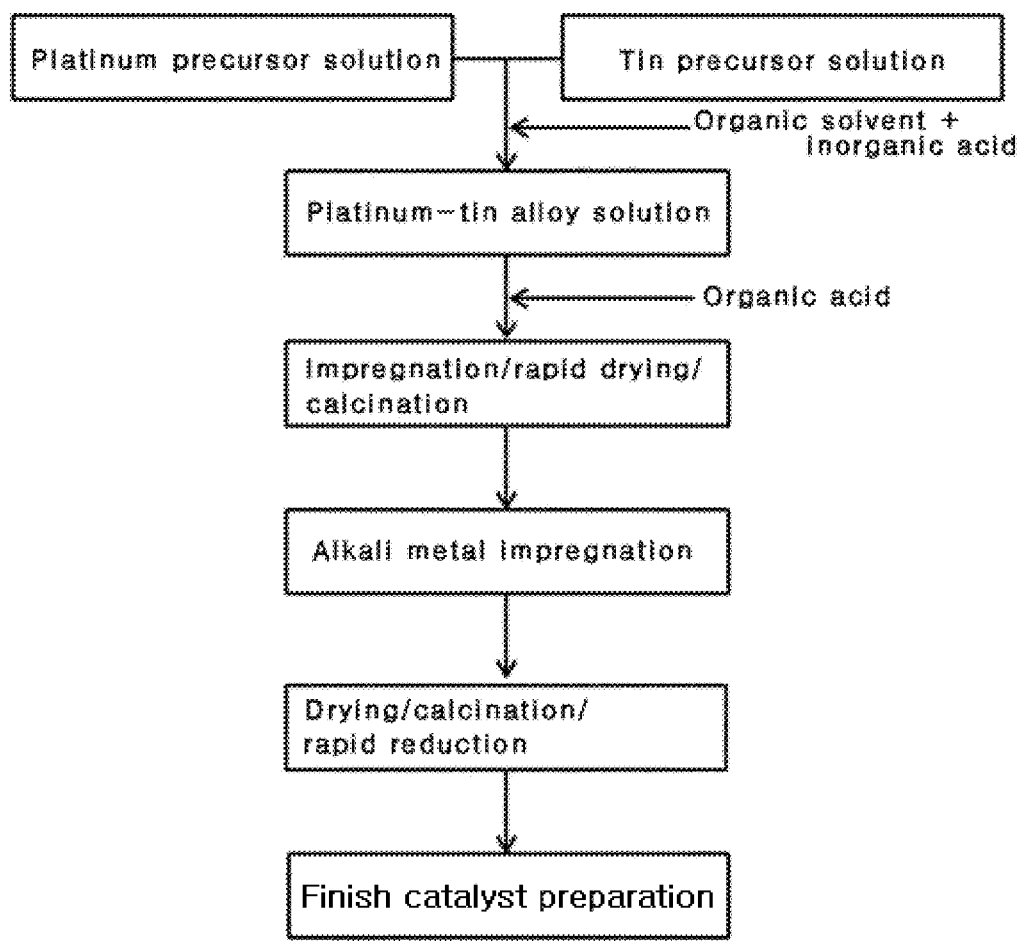

[FIG. 3]
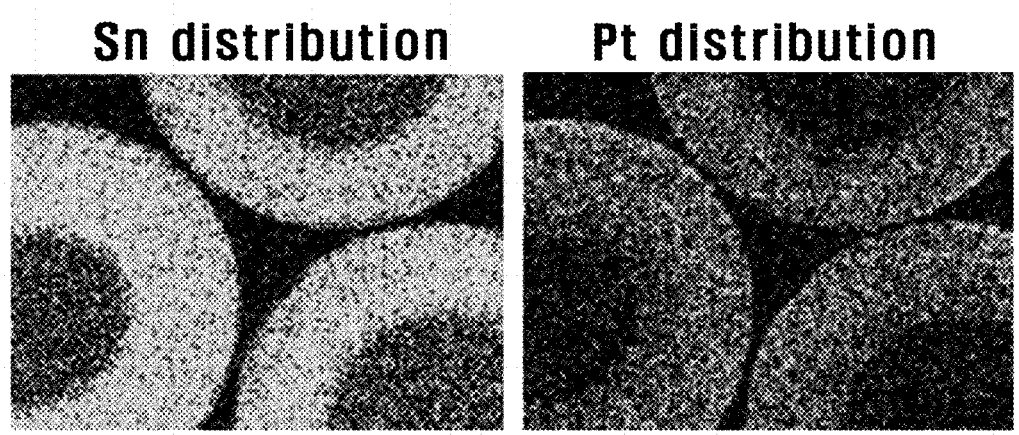

[FIG. 4]
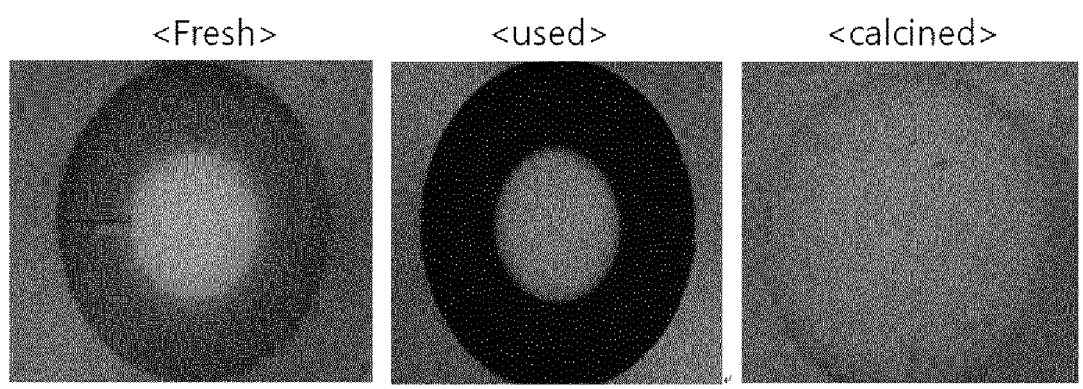
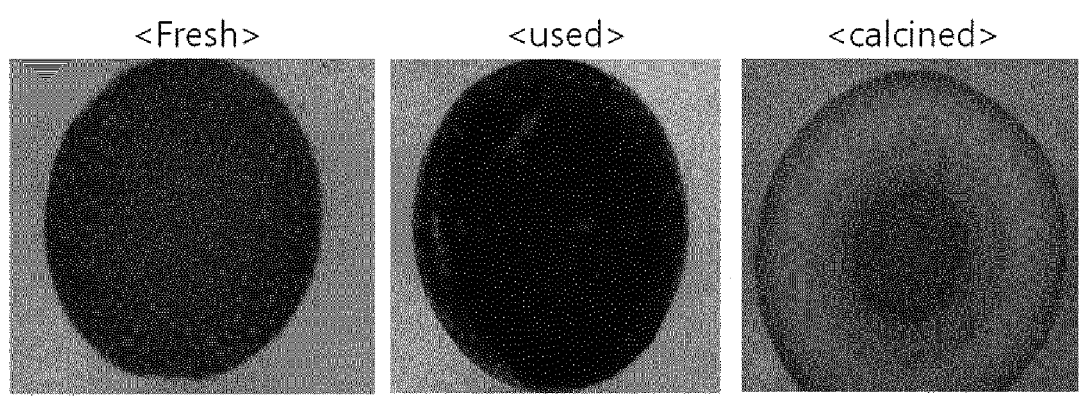

[FIG. 5]
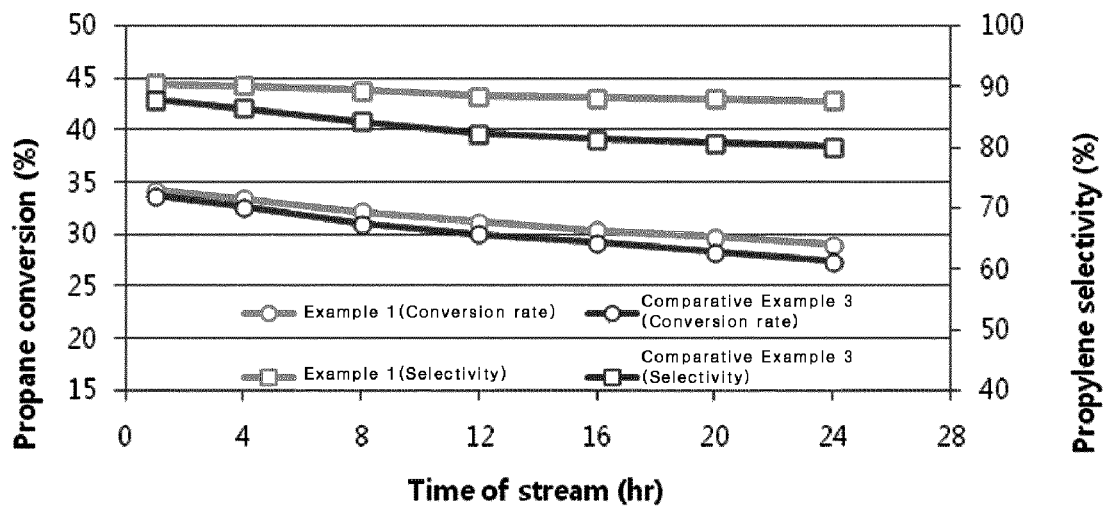
[FIG. 6]
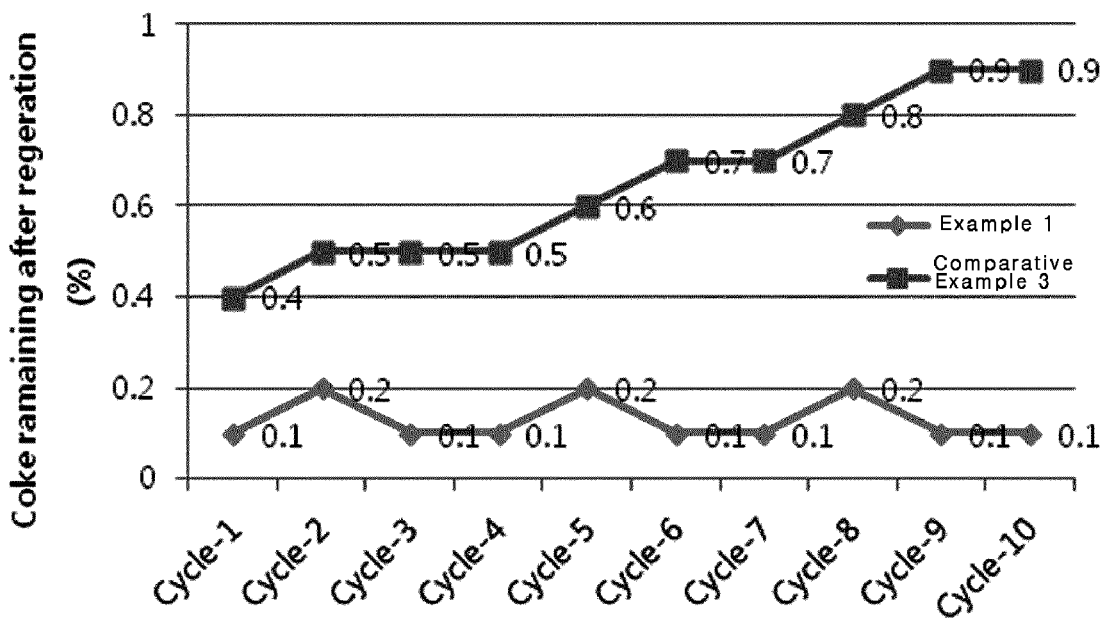

METHOD FOR PREPARING DEHYDROGENATION CATALYST FOR LINEAR CHAIN LIGHT HYDROCARBONS WITH HIGH REGENERATION EFFICIENCY

CROSS-REFERENCE TO RELATED APPLICATIONS

This application is a U.S. National Phase Application of International Application No. PCT/KR2018/000514, filed Jan. 11, 2018, which claims priority to Korean Application No. 10-2017-0058603, filed May 11, 2017, each of which are hereby incorporated by reference in their entirety.

TECHNICAL FIELD

The present invention relates to a method of manufacturing a dehydrogenation catalyst of straight-chain light hydrocarbons using a stabilized active metal complex, that is, to a dehydrogenation catalyst of straight-chain hydrocarbons in the range of $C_3$ to $C_4$. More specifically, the present invention relates to a technology of manufacturing a catalyst which contains metal components present in an alloy form within a predetermined thickness on the surface of a carrier and which has a high conversion rate, selectivity, and regeneration efficiency when used in dehydrogenation. Particularly, an organic solvent and an organic acid are used when metals are carried, thus manufacturing a catalyst exhibiting high dispersibility and alloy properties so that the alloy is present in a unique form in the catalyst using rapid drying and rapid reduction methods.

BACKGROUND ART

Light olefins are materials used in various commercial applications such as raw materials for plastics, synthetic rubbers, medicines, and chemical products. Typically, light olefins are extracted as byproducts generated when naphtha derived from crude oil is pyrolyzed, or are extracted from by-product gas of cracking reactions. However, the demand for light olefins in the world is increasing every year, but the production amount is limited by conventional production methods. Therefore, research on the manufacture of light olefins by dehydrogenation using catalysts is progressing steadily. Among this research, dehydrogenation catalysis has a merit in that a product having a high yield and a high purity is obtained compared to a conventional process, and is a reaction having a high manufacturing efficiency due to a simple process (Yuling Shan et al., Chem. Eng. J. 278 (2015), p 240). In general, various reactions occur depending on the carbon number of reactants in the dehydrogenation of hydrocarbons, and the main reaction thereof may be expressed as follows.

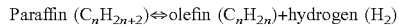

Paraffin $(C_nH_{2n+2})$⇔olefin $(C_nH_{2n})$+hydrogen $(H_2)$

In general, when thermal energy is applied to hydrocarbons, the bond strength between carbon and carbon (240 KJ/mol) is lower than the bond strength between carbon and hydrogen (360 KJ/mol). Accordingly, after the start of the thermodynamic reaction, a carbon-carbon cleavage reaction occurs first, resulting in the generation of byproducts and thus the low yield of the product. However, when a suitable catalyst is used, the carbon-carbon cleavage reaction may be minimized, which enables the dehydrogenation to thus secure the high yield and selectivity.

It has been reported to date that a shaped carrier having internal pores, such as gamma/theta/alpha alumina, zeolite, silica, and spinel-type metal aluminate, can be used in the dehydrogenation of light hydrocarbons. However, commercially, the carrier is mainly applied in the form of a catalyst in which an active component is carried in an alumina carrier. Typically, the conversion rate and selectivity of dehydrogenation are important determinants of catalyst selection, and the following is taken into consideration when designing catalysts. In the control of active points, since the dehydrogenation extent of platinum is very high, alkali metal is introduced. In addition, some transition metal is introduced in order to prevent deterioration of catalyst activity caused by carbon deposition. Further, with respect to mass transfer into catalyst particles and the dispersibility of the active material, the active material is uniformly distributed inside spherical particles having a diameter of 2 to 3 mm, thereby increasing the total conversion rate and suppressing a sintering phenomenon at high temperatures, which retards an activity decrease. Platinum or a Group VIII noble metal as an active component is mainly carried in silica, alumina, or silica-alumina, thus manufacturing the catalyst. The catalyst has a drawback in that metal particles are sintered at an early stage of the reaction due to the high-temperature reaction, thus decreasing the lifespan of the catalyst. When platinum or Group VIII noble metal is present alone in the catalyst, a rapid sintering phenomenon of the particles occurs due to high temperatures as the reaction progresses, and the catalyst is easily poisoned by the coke generated after the reaction. When an auxiliary metal is disposed next to the catalyst, since the auxiliary metal facilitates the easy transfer of the coke precursors adsorbed on the platinum to the carrier, it is very important that active metal species be made into an alloy state in the catalyst. Therefore, conventionally, in the dehydrogenation of paraffin, a composite catalyst, which includes two or three species and which is obtained by combining a Group VIII noble metal element such as platinum with one or more other metal components such as tin, gallium, indium, rhodium, ruthenium, palladium, cobalt, iron, germanium, potassium, and sodium, is used in order to improve the dispersibility and selectivity of the active metal of the catalyst and also to improve the lifespan of the catalyst (J. Catal., 320 (2014), p 52; Catal. Today, 111 (2006), p 133).

Meanwhile, studies on the active metals of catalysts and research on the carriers of these metals have been performed extensively. Particularly, the importance of the catalyst carrier is well disclosed in U.S. Pat. No. 7,432,406, Korean Patent No. 2002-0048142, and studies by Ke et al. (Chem. Eng. J. 284 (2016), p 1068), Zeeshan et al. (Korean J. Chem. Eng., 26(6), (2009), p 1528), Owen et al. (J. Mol. Catal., 79(1993), p 265), Bao et al. (Appl. Catal. A: Gen., 400 (2011), p 25), and Bing et al. (Appl. Catal. A: Gen., 533 (2017), p. 17). According to the results of the studies, the activity and the olefin selectivity of the catalyst are greatly influenced not only by the dispersibility of the metal but also by the characteristics of the catalyst carrier. Studies have been conducted on the use of materials such as silica, mesoporous silica (SBA-15, hydrotalcite ($MgAlO_x$), zinc aluminate ($ZnAl_2O_4$), zeolite, and magnesium-vanadium oxide ($MgO/V_2O_5$) as catalyst supports. These materials have a good effect on resistance to coke or product selectivity. However, when the amount of coke accumulated in the catalyst gradually increases as the reaction progresses, the micropores present in the catalyst are clogged by the coke, so that the active metals present therein become unable to participate in the reaction, resulting in deactivation. Further, since some of these materials must be manufactured using manufacturing methods such as hydrothermal synthesis or coprecipitation, the cost of manufacturing the raw material is high, the mesopore size is not easily controlled, and a separate particle-forming process is required for use in a commercial process. Therefore, there is a limit in that the manufacturing cost is high. Korean Patent No. 2000-0026638 reports that since the reaction of $C_5$ or smaller hydrocarbons proceeds at high temperatures, a large amount of coke is generated even in a short reaction time, accordingly, when reactants are easily discharged to the outside of the catalyst after the reactants come into contact with the active sites of the catalyst to cause the reaction, side reactions and coke deposition can be decreased.

Therefore, with respect to the internal pores of the catalyst, the micropores must be reduced, but the pores must be maintained, so that most of the pores form large pores. From this point of view, an alumina carrier which makes it relatively easy to control the pore size using only heat treatment is applied mainly to the catalyst carrier. Among them, it is known that gamma alumina is vulnerable to coke deposition due to the small pore size thereof and that side reactions occur due to acid sites of the carrier. Alpha alumina has a drawback in that since the dispersibility of the metal is lowered to induce coagulation of the metals, selectivity is favorable but the total conversion rate is low. Therefore, the alumina phase used in most documents describing the manufacture of light olefins, such as U.S. Pat. Nos. 4,717,779 and 4,914,075, Korean Patent Nos. 10-2005-0009290 and 10-2010-0078460, Jie et al. (Appl. Surf. Sci., 368 (2016) P233), and Bhari et al. (Catal. Today, 232(2014), p 40), is theta alumina, which is heat-treated at around 1000° C. The theta alumina has excellent effects on conversion rate and selectivity by minimizing the coagulation between metals because of its high ability to suppress side reactions by eliminating the acid sites using high-temperature heat treatment and its high ability to bind to metals. For catalyst regeneration, coke oxidation must be smoothly performed due to the characteristics of light hydrocarbon dehydrogenation to be regenerated in a short cycle, and it is preferable to regenerate the catalyst at the lowest possible temperature in order to prevent a phenomenon of rapid sintering of particles. The above-described catalyst regeneration characteristics greatly depend on the pore size of the carrier, the alloy state of platinum and tin, and the distribution pattern of platinum.

U.S. Pat. No. 4,716,143 discloses a catalyst in which Pt and Sn are concentrated at a depth of 100 microns from the outer periphery thereof but a predetermined concentration of Pt is included in the inside of the catalyst, that is, a catalyst having a Pt-gradation constitution. U.S. Pat. No. 4,786,625 discloses a structure in which Pt forms a shell on the outer periphery thereof and Sn is uniformly distributed throughout the catalyst.

DISCLOSURE

Technical Problem

According to the conventional technology, since the alloy form of platinum and tin is manufactured by sequentially carrying platinum and tin, the alloy form of platinum and tin depends only on the probability of contact of the two active materials. In addition to the optimum platinum/tin molar ratio of the target reaction, platinum is present alone, or another alloy having another platinum/tin molar ratio is present. In general, optimal results can be achieved only when platinum, which is an active site of dehydrogenation, and tin, which improves the stability of platinum, are present in an alloy form. However, the conventional technology has a problem in that since platinum is present alone or tin is present alone in addition to the platinum-tin alloy, side reactions occur during the reaction. The conventional technology also has the following problems: since a catalyst in which platinum and tin are uniformly distributed in the center of an alumina carrier is used, the catalyst activity is lowered due to carbon (coke) deposited in the alumina during the reaction, and the catalyst is not completely regenerated into an initial state due to coke which remains therein, and furthermore is not oxidized even when trying to remove the carbon using a calcination process.

Technical Solution

According to the present invention, in a dehydrogenation catalyst of light paraffinic hydrocarbons, active metals in a carrier are not distributed alone but remain constant in an alloy form, and this alloy is present between the surface of the catalyst and an inner core thereof at a predetermined thickness. In this structure, carbon deposits are not formed due to the absence of an alloy at the center of the catalyst during the dehydrogenation, and carbon deposits are located only at the outer periphery of the catalyst where the alloy is distributed. Therefore, it is an object of the present invention to provide a catalyst having greatly improved durability and a method of manufacturing the same by completely removing the carbon deposits from the inside of the catalyst after a catalyst regeneration process. The present invention is based on the recognition that a platinum-tin alloy ratio is not constant when an active metal is directly carried by a conventional technology. Platinum and tin are made into a composite in an organic solvent, and the composite is carried together with a predetermined amount of organic acid in a carrier so as to be distributed in a predetermined thickness from the surface of an alumina carrier, thereby completing the catalyst.

Advantageous Effects

According to the present invention, the same distribution of platinum and tin is obtained in a carrier by using a platinum-tin composite solution, and the conversion rate and selectivity are improved by keeping a platinum-tin alloy ratio constant. A catalyst is manufactured so that a platinum-tin alloy is not present in the carrier. Accordingly, carbon deposition is minimized inside the carrier during a reaction and the deposited coke is easily removed during a regeneration process after the reaction, thereby significantly improving the regeneration and durability of the catalyst.

DESCRIPTION OF DRAWINGS

FIG. 1 shows the state of catalysts of the conventional technology and the present invention after a reaction;

FIG. 2 shows a flowchart of steps of the method of the present invention;

FIG. 3 is a picture of electron probe microanalysis (EPMA) of the catalyst manufactured in Example 1 of the present invention;

FIG. 4 is comparative electron microscope pictures (video microscopy) showing the catalysts manufactured using the conventional technology and the present invention before and after regeneration;

FIG. 5 shows the propane conversion rate and the propylene selectivity according to the number of regeneration cycles of the catalysts using the catalysts manufactured in Example 1 and Comparative Example 3; and FIG. 6 shows a change in the amount of carbon accumulated in the catalyst according to the number of regeneration cycles of the catalysts using the catalysts manufactured in Example 1 and Comparative Example 3.

BEST MODE

The present invention relates to a dehydrogenation catalyst of straight-chain hydrocarbons in the range of $C_3$ to $C_4$, and also to a technology of manufacturing a catalyst which contains metal components present in an alloy form in a carrier in a predetermined thickness from the surface of the carrier. The dehydrogenation catalyst of light hydrocarbons is subjected to a relatively high-temperature reaction compared to heavy hydrocarbons, thus forming a large amount of coke due to thermal decomposition and other side reactions. Therefore, the mass transfer rate depending on the pore size and the pore volume of the carrier may be a major factor in the corresponding reaction. Further, when a gas hourly space velocity (GHSV), that is, an addition rate of reactants into a reactor, is high, the amount of carbon deposited in the catalyst rapidly increases. In the catalyst regeneration process that is periodically performed, since the deposited carbon must be easily removed, it is very important to control the pore distribution in the carrier. Platinum, which is an active metal directly participating in the reaction, is easily covered with coke when platinum is present alone in the carrier. Accordingly, a predetermined amount of auxiliary metal or alkali metal must always be present around platinum. When the auxiliary metal or alkali metal is distributed independently in the catalyst rather than around the platinum, adverse results are obtained in terms of both selectivity and durability. Therefore, it was concluded that the use of a catalyst satisfying the above conditions would suppress the side reaction in the dehydrogenation, thereby improving the durability and also the conversion rate and selectivity of the catalyst reaction. Surprisingly, the present inventors have found that when the active metals are not distributed alone in the carrier but are present in an alloy form in a predetermined thickness from the surface of the catalyst to the inside thereof in the case of the dehydrogenation catalyst of light paraffinic hydrocarbons, it is possible to manufacture a catalyst capable of greatly increasing the conversion rate of paraffin, olefin selectivity, and durability. The present invention provides a method of manufacturing a catalyst capable of controlling the distribution of an active metal in a predetermined thickness from the surface of the catalyst by carrying an alloy-type active metal formed using an organic solvent together with a predetermined amount of an organic acid and/or an inorganic acid. FIG. 1 shows the core technology of the present invention for comparison with a conventional technology, and FIG. 2 shows a flowchart of a method of manufacturing a catalyst, which comprehensively explains the method of the present invention.

1) Step of Manufacturing Stabilized Platinum-Tin Composite Solution

The composite solution of platinum and tin readily causes precipitation of platinum in air due to the high reducibility of tin. Therefore, selection of a solvent is very important in the manufacture of the composite solution. When water is used as the solvent, since tin reduces platinum, a platinum-tin precursor solution remains very unstable, and eventually platinum particles are precipitated, which makes the solution unusable as a precursor. Therefore, the present inventors manufactured a precursor solution that is maintained in a stable state over time using a solvent that does not reduce tin. First, the precursors of platinum and tin were added to the organic solvent when being mixed with each other so that the platinum-tin composite was not decomposed, and hydrochloric acid was added to manufacture an acidic solution. Then, an organic acid was added in order to increase the penetration speed into the inside of the carrier. In the case of the organic solvent, one or two among water, methanol, ethanol, butanol, acetone, ethyl acetate, acetonitrile, ethylene glycol, triethylene glycol, glycol ether, glycerol, sorbitol, xylitol, dialkyl ether, and tetrahydrofuran may be sequentially used, or may be used as a mixed solution. In the case of the organic acid, one or two among formic acid, acetic acid, glycolic acid, glyoxylic acid, oxalic acid, propionic acid, and butyric acid of carboxylic acids may be mainly used as a mixed solution. During the manufacture of the platinum-tin composite solution, the solution is aged in an inert gas atmosphere to thus suppress decomposition by oxygen and to achieve stabilization. Nitrogen, argon, and helium may be used as the inert gas, and nitrogen gas is preferably used.

2) Step of Manufacturing Catalyst using Stabilized Platinum-Tin Composite Solution and Alkali Metal In order to increase the pore size and the pore volume, the carrier is heat-treated in a calcination furnace at 1000 to 1050° C. for 1 to 5 hours, whereby gamma alumina is phase-changed to theta alumina to use. The heat treatment temperature is closely related to the crystal phase and the pore structure of the carrier. When the heat treatment temperature is 1000° C. or less, the crystal phase of alumina is in a state in which gamma and theta are mixed with each other, and the pore size of the carrier is small, and thus the diffusion rate of reactants in the carrier may be lowered. When the heat treatment temperature is 1050° C. or more, the crystal phase of alumina is in a state in which theta and alpha phases are mixed with each other, and thus the pore size is favorable to the reaction, but the dispersibility of the active metals distributed on the alpha alumina is lowered during a process of carrying the active metals. In the process of carrying the active metals, a platinum-tin composite solution is manufactured in an amount equivalent to the total pore volume of the carrier, and is impregnated in the carrier using a spray-carrying method. After the impregnation, an aging process is performed for a predetermined period of time in order to control the penetration depth of platinum and tin into alumina using an organic acid. After the aging process, a rapid drying process is performed while fluidizing the catalyst in an atmosphere of 150 to 250° C., thus removing most of the organic solvent remaining in the catalyst. Water remaining in the catalyst is completely removed via a drying process at 100 to 150° C. for 24 hours. The reason for performing rapid drying is to prevent the platinum-tin composite solution from diffusing into the carrier together with an inorganic or organic acid solvent over time when the platinum-tin composite solution is carried in the alumina carrier. Rapid drying at a temperature lower than 150° C. is insignificant for the fixing of metals, and rapid drying at 250° C. or higher may cause coagulation of metal particles due to the decomposition reaction of an organic solvent. After drying, an organic material is removed under a nitrogen atmosphere at 250 to 400° C., followed by a calcination process in an ambient atmosphere at 400 to 700° C. When the heat treatment is performed at 400° C. or lower, the carried metal may not be converted into metal oxide species. When the heat treatment is performed at 700° C. or higher, an intermetallic coagulation phenomenon occurs, and the catalyst activity is not high considering the amount of the catalyst. After calcination, a step for carrying alkali metal is performed in order to suppress the catalyst side reaction. First, potassium is carried in the internal pores of the carrier using the same spray-carrying method as in the case of the above-mentioned platinum-tin composite solution, and a drying process at 100 to 150° C. for 24 hours and a calcination process in an ambient atmosphere at a temperature in the range of 400 to 700° C. are performed. Finally, after the calcination, a reduction process is performed using a hydrogen/nitrogen mixed gas (a range of 4%/96% to 100%/0%) at a temperature in the range of 400 to 600° C., thus obtaining a final catalyst. When a reduction temperature is lower than 400° C. during the reduction process, the metal oxide species may not be completely reduced, and two or more kinds of metal particles may be present as individual metals rather than in an alloy form. Further, when the reduction temperature is higher than 600° C., coagulation and sintering occur between two or more kinds of metal particles, and as a result, the catalyst activity may be lowered as the number of active sites decreases. The reduction is performed using a rapid high-temperature reduction method in which a nitrogen atmosphere is maintained until a predetermined temperature is reached and hydrogen gas is injected to perform the reduction when the predetermined temperature is reached, instead of a temperature-raising reduction method in which reduction is performed using hydrogen gas from a temperature-raising step. When the reduction is performed using the temperature-raising reduction method, there is a problem in that since the reduction temperatures of platinum and tin are different from each other, they are present in the form of individual metals in the catalyst after the reduction, so that the role of tin cannot be maximized in terms of coke suppression and durability.

The performance of the catalyst manufactured as described above is evaluated as follows. Conversion of light paraffin hydrocarbons into olefins may be performed using a gas-phase reaction under a condition of 500 to 680° C., preferably 570° C., 0 to 2 atm, preferably 1.5 atm, and a paraffin hydrocarbon GHSV (gas hourly space velocity) of 5000 to 10000 h$^{-1}$, preferably 6000 to 8000 h$^{-1}$, by diluting hydrocarbons having 2 to 5 carbon atoms, preferably 3 to 4 carbon atoms, including paraffins, isoparaffins, and alkyl aromatics, with hydrogen using the dehydrogenation catalyst according to the present invention. The reactor for producing olefins using the dehydrogenation is not particularly limited, but a fixed-bed catalytic reactor in which the reactor is filled with a catalyst may be used. Further, since dehydrogenation is an endothermic reaction, it is important that the catalyst reactor always be maintained under adiabatic conditions. For the dehydrogenation process of the present invention, it is important to perform the reaction while maintaining a reaction temperature, a pressure, and a liquid hourly space velocity, which are reaction conditions, within a suitable range. When the reaction temperature is low, the reaction does not proceed. When the reaction temperature is very high, the reaction pressure is increased in proportion thereto, and side reactions such as coke formation and a cracking reaction occur.

MODE FOR INVENTION

Example 1: Manufacture of Catalyst Using Simultaneous Platinum-Tin Impregnation Method With respect to the carrier used in Example 1, a gamma alumina carrier (Manufacturer: BASF in Germany, specific surface area: 210 m$^2$/g, pore volume: 0.7 cm$^3$/g, average pore size: 8.5 nm) was calcinated at 1020° C. for 5 hours so as to be phase-changed into theta alumina, and the resultant theta alumina carrier was used. The phase-changed theta alumina has physical properties including a specific surface area of 92 m$^2$/g, a pore volume of 0.41 cm$^3$/g, and an average pore size of 12 nm. Chloroplatinic acid ($H_2PtCl_6$) was used as a platinum precursor and tin chloride ($SnCl_2$) was used as a tin precursor. The chloroplatinic acid in an amount equivalent to 0.4 wt % of the total weight of the catalyst and tin chloride were mixed in a nitrogen atmosphere so that the molar ratio of platinum/tin was 1.1. Thereafter, a solvent was added to the platinum-tin mixture so that the amount of the solvent corresponds to the total pore volume of the carrier, thus dissolving the mixture. The solvent that was used was manufactured using 97 wt % of ethanol and 3 wt % of hydrochloric acid. In addition, glyoxylic acid was mixed therewith in an amount equivalent to 3 wt % of the total amount of the solvent in order to realize flowability of a platinum-tin alloy solution in the carrier. Thereafter, the theta alumina carrier undergoing phase changing was impregnated with the manufactured platinum-tin composite solution using an initial wetting method. After the impregnation, an aging process was performed at room temperature for about 30 minutes, followed by a continuous rapid drying process at 170° C., thereby removing 90% or more of the carried organic solvent. Thereafter, drying was performed at 120° C. for 24 hours to thus completely remove moisture remaining in the catalyst, followed by heat treatment at 600° C. for 4 hours in an ambient atmosphere, thereby fixing the active metal. Next, potassium nitrate ($KNO_3$) was carried in an amount of 1.0 wt % based on the total weight of the catalyst in the internal pores of alumina containing platinum and tin using an initial wetting method. The composition in which metal was carried was heat-treated in an ambient atmosphere at 570° C. for 4 hours, thus manufacturing a metal-carried catalyst. The reduction process of the catalyst was performed in a stepwise manner, the temperature was increased to 570° C. in a nitrogen atmosphere, and then the catalyst was exposed to a flowing hydrogen/nitrogen mixed gas (4%/96%) for 4 hours, thereby manufacturing the catalyst. The states of platinum and tin of the catalyst manufactured in Example 1 are shown in FIG. 3 through electron probe microanalysis (EPMA). As a result, it was confirmed that the position and distribution of platinum and tin in the catalyst were maintained constant.

Example 2: Manufacture of Catalyst Using Simultaneous Platinum-Tin Impregnation Method In Example 2, a catalyst was manufactured using the same method as in Example 1, except that the ratio of ethanol and inorganic acid was 93 wt %:7 wt % when a platinum-tin composite solution was manufactured. Hydrochloric acid, nitric acid, or sulfuric acid may be applied as the inorganic acid.

Example 3: Manufacture of Catalyst Using Simultaneous Platinum-Tin Impregnation Method In Example 3, a catalyst was manufactured using the same method as in Example 1, except that fluidization was performed while a rapid drying temperature was maintained at 100° C. when the catalyst was manufactured.

Comparative Example 1: Manufacture of Catalyst Using Simultaneous Platinum-Tin Impregnation Method In Comparative Example 1, a catalyst was manufactured using the same method as in Example 1, except that the catalyst was dried at a relatively low temperature of 100° C. without a rapid drying process.

Comparative Example 2: Manufacture of Catalyst Using Simultaneous Platinum-Tin Impregnation Method In Comparative Example 2, a catalyst was manufactured using the same method as in Example 1, except that a reduction process after drying/calcination process in the manufacture of the catalyst was performed in a temperature-raising atmosphere.

Comparative Example 3: Manufacture of Catalyst Using Sequential Impregnation Method of Platinum and Tin With respect to the carrier used in Comparative Example 3, as in Example 1, gamma alumina was calcinated at 1050° C. for 2 hours so as to be phase-changed into theta alumina, and the resultant theta alumina was used. Chloroplatinic acid ($H_2PtCl_6$) was used as a platinum precursor. Platinum in an amount equivalent to 0.4 wt % of the total weight of the catalyst was diluted in deionized water in an amount equivalent to the total pore volume of the carrier and in the inorganic acid in an amount equivalent to 5 wt % of the total amount of the solvent, and was then impregnated in a carrier using an initial wetting method. The composition in which platinum was carried was heat-treated in an ambient atmosphere at 600° C. for 4 hours, thus fixing active metal. Thereafter, tin chloride ($SnCl_2$), used as a tin precursor so that a molar ratio of platinum and tin was 1.1, was diluted in the deionized water and the inorganic acid in an amount equivalent to 5 wt % of the total amount of the solvent, thus being carried in the internal pores of the platinum-carried alumina using an initial wetting method. The composition in which metal was carried was heat-treated in an ambient atmosphere at 600° C., thus fixing active metal. Thereafter, potassium nitrate ($KNO_3$) was carried in an amount of 0.7 wt % based on the total weight of the catalyst in internal pores of alumina containing platinum and tin using an initial wetting method. The composition in which metal was carried was heat-treated in an ambient atmosphere at 570° C. for 4 hours, thus manufacturing a metal-carried catalyst. The reduction of the catalyst was maintained for 4 hours using a hydrogen/nitrogen mixed gas (4%/96%), thereby manufacturing the catalyst.

Comparative Example 4: Manufacture of Catalyst Using Sequential Impregnation Method of Platinum And Tin In Comparative Example 4, a catalyst was manufactured using the same method as in Comparative Example 3, except that the inorganic acid which had been added in an amount of 5 wt % based on the total amount of the solvent was not added when platinum and tin were carried.

Experimental Example 1: Evaluation of Catalyst Performance

The dehydrogenation was performed in order to measure the catalyst activity, and a reactor was evaluated using a fixed-bed reaction system. 3.0 g of the catalyst was charged in a tubular reactor, and hydrogen gas was allowed to flow at a constant rate of 1000 cc/min, whereby the catalyst was reduced at 570° C. for 1 hour. Subsequently, the temperature of the reactor was kept constant at 570° C., which was the reaction temperature, a mixed gas of propane gas and hydrogen, which were raw materials used in the reaction, was continuously supplied to the reactor at a constant volume ratio of 6:4, and a gas hourly space velocity was constantly fixed at 8100 $h^{-1}$. Further, hydrogen sulfide gas in an amount equivalent to 100 ppm of the total amount of reactants was further injected in order to suppress the side reaction occurring during the catalytic reaction. The reaction pressure was constantly maintained at 1.5 atm using a pressure regulator. After the reaction had progressed for 1 hour and 4 hours, generated materials were migrated to a GC (gas chromatograph) through an injection line wrapped with hot wires, and quantitative analysis was performed using a FID (flame ionization detector) and a TCD (thermal conductivity detector). In the case of the regeneration experiment, after the reaction for 24 hours, purging was performed using nitrogen gas for 5 minutes, and then the coke was removed using 5%/95% oxygen/nitrogen balance gas at 570° C. for 3 hours. Thereafter, hydrogen gas was allowed to flow at a constant rate of 1000 cc/min to thus reduce the catalyst again. The above procedure was defined as '1 cycle', and the catalyst activity was evaluated for a total of '10 cycles'. The conversion rate of propane and the propylene selectivity for the product were calculated based on the following criteria, and the activities of the catalysts were compared to each other using the yield of propylene obtained thereby.

Conversion rate of propane (%)=[number of moles of propane before reaction−number of moles of paraffin after reaction]/[number of moles of propane paraffin]×100

Selectivity of propylene (%)=[number of moles of propylene in product]/[number of moles of product]×100

Yield of propylene (%)=[conversion rate of propane]×[selectivity of propylene]/100

The activity tests of the catalysts manufactured in Examples 1 to 3 and Comparative Examples 1 to 4 are shown in Table 1.

TABLE 1

| Classification | Distribution of metal in carrier (radius of 800 μm) | | Propane conversion rate (%) | | Propylene selectivity (%) | | Propylene yield (%) | | With of yield decrease (%) |
|---|---|---|---|---|---|---|---|---|---|
| | Platinum (μm) | Tin (μm) | 1 hr | 4 hr | 1 hr | 4 hr | 1 hr | 4 hr | |
| Example 1 | 500 | 500 | 34.2 | 34.0 | 90.4 | 88.5 | 30.9 | 30.1 | −0.8 |
| Example 2 | 800 | 800 | 34.0 | 32.3 | 84.4 | 82.6 | 28.7 | 26.7 | −2.0 |
| Example 3 | 650 | 500 | 33.0 | 31.2 | 83.7 | 81.6 | 27.6 | 25.5 | −2.2 |
| Comparative Example 1 | 700 | 600 | 33.3 | 31.3 | 87.8 | 82.3 | 29.2 | 25.8 | −3.5 |
| Comparative Example 2 | 500 | 500 | 25.7 | 24.2 | 81.2 | 79.7 | 20.9 | 19.3 | −1.6 |
| Comparative Example 3 | 800 | 800 | 32.3 | 31.6 | 86.1 | 84.8 | 27.8 | 26.8 | −1.0 |
| Comparative Example 4 | 600 | 400 | 29.9 | 26.4 | 86.3 | 84.2 | 25.8 | 22.2 | −3.6 |

Results

As shown in Table 1, the catalyst of Example 1, in which platinum and tin were impregnated in a predetermined thickness in the carrier in an alloy form, exhibited the best activity in terms of conversion rate and selectivity. In the case of Example 1, platinum and tin were distributed in the same thickness of 500 μm on the surface of the carrier using a rapid drying process and were present in the form of a platinum-tin alloy, so that side reactions due to the use of platinum or tin alone were suppressed, thereby exhibiting a high conversion rate and selectivity. According to various non-illustrated embodiments, similar results as those in Example 1 may be obtained when platinum and tin are distributed in the same thickness of 300 to 500 μm or less on the surface of the carrier.

In the case of Example 2, since the content of the inorganic acid that was added was increased, platinum and tin were uniformly present in the carrier. Accordingly, the number of times of contact between the reactant and the platinum-tin alloy was increased and dehydrogenation proceeded relatively well. In Example 2, it could be confirmed that the conversion rate was similar, but selectivity was low compared to Example 1. In the case of Example 3, the rapid drying process temperature of Example 1 was lowered, and thus platinum and tin were not fixed in a predetermined thickness to the surface of the carrier, but were separated. Since platinum was present alone, the side reaction proceeded strongly. Accordingly, selectivity was low, which leads to rapid deactivation. In Comparative Example 1, since the catalyst was manufactured without a rapid drying process, platinum and tin were distributed differently, exhibiting a relatively low conversion rate and durability. In Comparative Example 2, the activity was lower than that of other catalysts because platinum and tin were reduced at different temperatures as a result of the temperature-raising reduction rather than rapid reduction. The reduction temperature of platinum was 200 to 300° C., which is lower than 400 to 500° C., which is the reduction temperature of tin. Accordingly, when the reduction is performed using the temperature-raising method, the distributions of platinum and tin coincide with each other, but the reductions thereof separately occur, thus exhibiting low activity, as in Comparative Example 2. The catalysts of Comparative Examples 3 and 4 were manufactured using a sequential impregnation method. In the case of Comparative Example 4, the distributions of platinum and tin were not consistent with each other as the amount of the inorganic acid added decreased. Both cases showed a low conversion rate and selectivity compared to a simultaneous impregnation method, and Comparative Example 4, where the distributions of platinum and tin did not coincide with each other, exhibited rapid deactivation.

Experimental Example 2: Evaluation of Catalyst Activity

The dehydrogenation of reactants was performed for 12 hours under the same conditions as in Experimental Example 1 using the catalysts manufactured in Example 1 and Comparative Example 3, and the results are shown in FIG. 5 and Table 2 below.

Table 2: Results of Activity Evaluation of the Catalysts Manufactured in Example 1 and Comparative Example 3 for Each Time

TABLE 2

| T.O.S (hr) | Propane conversion rate (%) | | Propylene selectivity (%) | | Propylene yield (%) | |
|---|---|---|---|---|---|---|
| | Example 1 | Comparative Example 3 | Example 1 | Comparative Example 3 | Example 1 | Comparative Example 3 |
| 1 | 34.2 | 32.3 | 90.4 | 86.1 | 30.9 | 27.8 |
| 4 | 34.0 | 31.6 | 88.5 | 84.8 | 30.1 | 26.8 |
| 8 | 33.7 | 31.0 | 88.4 | 84.5 | 29.8 | 26.2 |
| 12 | 33.6 | 30.6 | 88.1 | 84.0 | 29.6 | 25.7 |
| 16 | 33.3 | 30.1 | 87.5 | 83.6 | 29.1 | 25.2 |
| 20 | 33.0 | 29.7 | 87.3 | 83.4 | 28.8 | 24.8 |
| 24 | 32.6 | 29.1 | 87.2 | 83.2 | 28.4 | 24.2 |

As shown in Table 2, in the case of Example 1, platinum and tin were identically distributed in a predetermined thickness using the rapid drying process, thus exhibiting a conversion rate, selectivity, and durability higher than those in Comparative Example 3.

In the case of Comparative Example 3, since the probability that platinum and tin were present as an alloy was relatively low due to sequential impregnation compared to Example 1, the extent of side reactions was increased due to the presence of platinum alone, thus lowering selectivity and hastening deactivation.

Experimental Example 3: Evaluation of Catalyst Regeneration Performance

After the dehydrogenation of the reactants was performed for 12 hours under the same conditions as in Experimental Example 1 using the catalysts manufactured in Example 1 and Comparative Example 3, the catalysts were subjected to calcination and reduction processes and then added back to the reactor to perform dehydrogenation. The activity was evaluated while the above reaction was repeated 10 times in total, and the results are shown in FIG. 6 and Table 3 below. Further, thermogravimetric analysis was performed with respect to the residual carbon content in the catalyst after each calcination process when 10 cycles were repeated, and the results are shown in Table 3.

Table 3: Results of Activity Evaluation for the Number of Regeneration Cycles of Catalysts Manufactured in Example 1 and Comparative Example 1 and Analysis of Residual Carbon Content in the Catalyst

TABLE 3

| Number of regeneration cycles (cycles) | Propane conversion rate (%) | | Propylene selectivity (%) | | Propylene yield (%) | | Amount of residual coke after regeneration (%) | |
|---|---|---|---|---|---|---|---|---|
| | Example 1 | Comparative Example 3 | Example 1 | Comparative Example 3 | Example 1 | Comparative Example 3 | Example 1 | Comparative Example 3 |
| 1 | 32.6 | 29.1 | 87.2 | 83.2 | 28.4 | 24.2 | 0.1 | 0.4 |
| 2 | 32.8 | 27.9 | 87.4 | 79.4 | 28.7 | 22.2 | 0.2 | 0.5 |
| 3 | 32.3 | 27.5 | 87.6 | 79.5 | 28.3 | 21.9 | 0.1 | 0.5 |
| 4 | 32.6 | 27.0 | 87.7 | 79.6 | 28.6 | 21.5 | 0.1 | 0.5 |
| 5 | 31.9 | 26.7 | 87.5 | 79.1 | 27.9 | 21.1 | 0.2 | 0.6 |
| 6 | 32.3 | 26.6 | 87.2 | 79.0 | 28.2 | 21.0 | 0.1 | 0.7 |
| 7 | 31.7 | 26.8 | 87.2 | 79.3 | 27.6 | 21.3 | 0.1 | 0.7 |
| 8 | 31.4 | 26.0 | 87.0 | 79.0 | 27.3 | 20.5 | 0.2 | 0.8 |
| 9 | 31.8 | 26.1 | 87.2 | 78.5 | 27.7 | 20.5 | 0.1 | 0.9 |
| 10 | 31.5 | 25.4 | 87.1 | 78.4 | 27.4 | 19.9 | 0.1 | 0.9 |

FIG. 4 is comparative pictures showing electron probe microanalysis (EPMA) of the catalysts manufactured in Example 1 and Comparative Example 3 of the present invention. When platinum and tin are thinly distributed in the carrier, it can be seen that the coke deposited on the inside is completely oxidized and disappears as the catalyst is subjected to the calcination-reduction process after the use of the catalyst. However, when platinum and tin are uniformly distributed in the carrier, it can be confirmed that even when the calcination-reduction process is performed after the use of the catalyst, the coke deposited deep inside the carrier is not completely oxidized, but remains therein. In Table 3, after the regeneration of the catalyst of Example 1 and the catalyst of Comparative Example 3, the difference in the residual coke amount was significant. As the number of regeneration cycles increased, the amount of residual coke remained low after regeneration of the catalyst in Example 1. However, it can be confirmed that the residual coke was gradually accumulated in the case of the catalyst of Comparative Example 3. Since the coke in the central portion of the catalyst was not completely oxidized, the conversion rate of propane gradually decreased as the number of regeneration cycles increased.

The above-described results show that the distribution of the platinum-tin alloy in a predetermined thickness on the outer surface of the carrier is more effective for the regeneration of the catalyst compared to the uniform distribution of platinum and tin in the carrier.

The invention claimed is:

1. A dehydrogenation catalyst for use in dehydrogenation of straight-chain hydrocarbon gas in a range of C3 to C4, the dehydrogenation catalyst comprising:
    platinum, an auxiliary metal, and an alkali metal which are carried in a phase-changed carrier,
    wherein the platinum and the auxiliary metal form a single complex and are present in an alloy form within a predetermined thickness from an outer periphery of the catalyst.

2. The dehydrogenation catalyst of claim 1, wherein the predetermined thickness is realized by a rapid heat-treatment process and a rapid drying process of the single complex using an organic acid and an inorganic acid.

3. The dehydrogenation catalyst of claim 1, wherein the catalyst is obtained using a process further including a calcination step and a reduction step, and the reduction step is realized by a high-temperature rapid reduction process.

4. The dehydrogenation catalyst of claim 1, wherein the predetermined thickness is 300 to 500 μm thick from the outer periphery of the catalyst.

5. The dehydrogenation catalyst of claim 2, wherein the inorganic acid is a hydrochloric acid, a nitric acid, or a sulfuric acid.

6. The dehydrogenation catalyst of claim 2, wherein the organic acid further includes one among a formic acid, an acetic acid, a glycolic acid, a glyoxylic acid, an oxalic acid, a propionic acid, and a butyric acid, or a mixture including two thereof.

7. The dehydrogenation catalyst of claim 1, wherein the auxiliary metal is selected from the group consisting of tin, germanium, gallium, and manganese.

8. The dehydrogenation catalyst of claim 1, wherein the alkali metal is selected from the group consisting of potassium, sodium, and lithium.

9. The dehydrogenation catalyst of claim 1, wherein the carrier is selected from the group consisting of alumina, silica, zeolite, and a composite component thereof.

* * * * *